US00PP27988P3

(12) United States Plant Patent
van Dijk

(10) Patent No.: US PP27,988 P3
(45) Date of Patent: May 9, 2017

(54) *HYDRANGEA* PLANT NAMED 'DICUR'

(50) Latin Name: *Hydrangea macrophylla*
Varietal Denomination: DICUR

(71) Applicant: Roy Robin van Dijk, De Lier (NL)

(72) Inventor: Roy Robin van Dijk, De Lier (NL)

(73) Assignee: Dijk van Dijk B.V., De Lier (NL)

( * ) Notice: Subject to any disclaimer, the term of this patent is extended or adjusted under 35 U.S.C. 154(b) by 3 days.

(21) Appl. No.: 14/756,533

(22) Filed: Sep. 15, 2015

(65) Prior Publication Data

US 2017/0079174 P1 Mar. 16, 2017

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — C. A. Whealy

(57) ABSTRACT

A new and distinct cultivar of *Hydrangea* plant named 'DICUR', characterized by its upright to outwardly spreading and mounding plant habit; moderately vigorous growth habit; freely branching habit; strong and sturdy stems; mophead-type inflorescences with numerous white-colored sterile flowers with incurved sepals giving a curly appearance to the flowers; and good postproduction longevity.

3 Drawing Sheets

Botanical designation: *Hydrangea macrophylla.*
Cultivar denomination: 'DICUR'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'DICUR'.

The new *Hydrangea* plant is a naturally-occurring whole plant mutation of *Hydrangea macrophylla* 'Schneeball', not patented. The new *Hydrangea* plant was discovered and selected by the Inventor as a single flowering plant from within a population of plants of 'Schneeball' grown in a controlled greenhouse environment in De Lier, The Netherlands in February, 2011.

Asexual reproduction of the new *Hydrangea* plant by vegetative terminal cuttings in a controlled greenhouse environment in De Lier, The Netherlands since March, 2012 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DICUR'. These characteristics in combination distinguish 'DICUR' as a new and distinct *Hydrangea* plant:

1. Upright to outwardly spreading and mounding plant habit.

2. Moderately vigorous growth habit.
3. Freely branching habit.
4. Strong and sturdy stems.
5. Mophead-type inflorescences with numerous white-colored sterile flowers with incurved sepals giving a curly appearance to the flowers.
6. Good postproduction longevity.

Plants of the new *Hydrangea* can be compared to plants of the mutation parent, 'Schneeball'. Plants of the new *Hydrangea* differ primarily from plants of 'Schneeball' in sepal aspect as sepals of plants of 'Schneeball' are flat and not incurved.

Plants of the new *Hydrangea* can also be compared to plants of *Hydrangea macrophylla* 'Wudu', not patented. In side-by-side comparisons conducted in De Lier, The Netherlands, plants of the new *Hydrangea* differed primarily from plants of 'Wudu' in sepal aspect as sepals of plants of 'Wudu' are flat and not incurved.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'DICUR' grown in a container.

The photograph on the second sheet is a close-up view of the upper (left) and lower (right) surfaces of typical leaves of 'DICUR'.

The photograph on the third sheet is a close-up view of a typical inflorescence of 'DICUR'.

DETAILED BOTANICAL DESCRIPTION

Plants used in the aforementioned photographs and in the following description were grown during the winter in 14-cm containers in a glass-covered greenhouse in De Lier, The Netherlands and under cultural practices typical of commercial *Hydrangea* production. During the production of the plants, day temperatures averaged 19° C., night temperatures averaged 21° C. and lightly levels were about 4,000 lux. Plants of the new *Hydrangea* were pinched one time and were one year old when the photographs and description were taken. In the following description, color references are made to The Royal Horticultural Society Colour Chart, 2007 Edition, except where general terms of ordinary dictionary significance are used.

Botanical description: *Hydrangea macrophylla* 'DICUR'.

Parentage: Naturally-occurring whole plant mutation of *Hydrangea macrophylla* 'Schneeball', not patented.

Propagation:

*Type cutting*.—By vegetative terminal cuttings.

*Time to initiate roots, summer*.—About 12 days at temperatures about 22° C.

*Time to initiate roots, winter*.—About two weeks at temperatures about 20° C.

*Time to produce a rooted young plant, summer*.—About four weeks at temperatures about 22° C.

*Time to produce a rooted young plant, winter*.—About one month at temperatures about 22° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright, outwardly spreading and mounding plant habit; flattened globular in overall shape; strong and sturdy stems; moderately vigorous growth habit.

*Plant height*.—About 26 cm.

*Plant diameter or area of spread*.—About 48.5 cm.

Lateral branch description:

*Branching habit*.—Freely branching habit with about ten lateral branches per plant; pinching enhances lateral branch development.

*Length*.—About 18.4 cm.

*Diameter*.—About 6 mm.

*Internode length*.—About 6.5 cm.

*Strength*.—Strong, sturdy.

*Aspect*.—About 45° from vertical.

*Texture*.—Smooth, glabrous; fully developed, woody.

*Luster*.—Moderately glossy.

*Color, developing*.—Close to 144B; at the nodes, slightly tinged with close to N187A.

*Color, fully developed*.—Close to N199B.

*Lenticels*.—Density: Medium, about five per $cm^2$. Length: About 3 mm. Width: About 1 mm. Color: Close to 187A.

Leaf description:

*Arrangement*.—Opposite, simple.

*Length*.—About 11.4 cm.

*Width*.—About 8.8 cm.

*Shape*.—Broadly ovate to broadly elliptic.

*Apex*.—Broadly apiculate.

*Base*.—Broadly attenuate.

*Margin*.—Serrate.

*Texture, upper and lower surfaces*.—Slightly rugose, glabrous.

*Luster, upper and lower surfaces*.—Slightly glossy.

*Venation pattern*.—Pinnate.

*Color*.—Developing leaves, upper surface: Close to 143C. Developing leaves, lower surface: Close to 146A. Fully developed leaves, upper surface: Darker than between N137A and 147A; venation, close to between 144A and 146A. Fully developed leaves, lower surface: Close to 146A; venation, close to 144C.

*Petioles*.—Length: About 2.6 cm. Diameter: About 4 mm. Texture, upper and lower surfaces: Smooth, glabrous. Luster, upper and lower surfaces: Glossy. Color, upper and lower surfaces: Close to 144A.

Flower description:

*Flower type and habit*.—Showy rotate sterile flowers and small, inconspicuous rotate fertile flowers arranged on mophead-type terminal panicles; panicles flattened globular in shape; sterile flowers face upright to outwardly to slightly dropping and fertile flowers mostly upright.

*Fragrance*.—Faintly fragrant, pleasant.

*Natural flowering season*.—In the garden, plants flower continuously from the late spring to late summer in The Netherlands. Flower dormancy can be broken by giving a two-month cold treatment.

*Flower longevity*.—Good postproduction longevity; sterile flowers maintain good substance for about six weeks on the plant, sterile flowers persistent; fertile flowers last about one week on the plant, fertile flowers not persistent.

*Quantity of flowers*.—Freely flowering habit; about 120 sterile flowers per panicle and about 14 fertile flowers per panicle.

*Panicle height*.—About 6.6 cm.

*Panicle diameter*.—About 11.5 cm.

*Sterile flower buds*.—Length: About 4 mm. Diameter: About 4 mm. Shape: Globular. Color: Close to 144D.

*Fertile flower buds*.—Length: About 3 mm. Diameter: About 3 mm. Shape: Globular. Color: Close to 145A.

*Sterile flower diameter*.—About 1.8 cm.

*Sterile flower depth* (*height*).—About 6 mm.

*Sterile flower shape*.—Rotate.

*Fertile flower diameter*.—About 7 mm.

*Fertile flower depth* (*height*).—About 2 mm.

*Petals, sterile flowers*.—Quantity and arrangement: Four in a single whorl. Length: About 3 mm. Width: About 2 mm. Shape: Ovate. Apex: Acute. Base: Broadly cuneate. Margin: Entire. Texture, upper and lower surfaces: Smooth, glabrous. Luster, upper and lower surfaces: Matte. Color: When opening, upper and lower surfaces: Close to NN155D. Fully opened, upper and lower surfaces: Close to NN155D; color does not change with development.

*Petals, fertile flowers*.—Quantity and arrangement: Five in a single whorl. Length: About 2 mm. Width: About 1.2 mm. Shape: Ovate, concave. Apex: Acute. Base: Cuneate. Margin: Entire. Texture, upper and lower surfaces: Smooth, glabrous. Luster, upper and lower surfaces: Matte. Color: When opening, upper and lower surfaces: Close to 157D. Fully opened, upper and lower surfaces: Close to 157D; color does not change with development.

*Sepals, sterile flowers*.—Quantity and arrangement: Three to four in a single whorl. Length: About 1 cm. Width: About 1.2 cm. Shape: Orbicular to reniform;

towards the margins, incurved, giving the flowers a curly appearance. Apex: Rounded. Base: Broadly cuneate. Margin: Crenate. Texture, upper and lower surfaces: Smooth, glabrous. Luster, upper and lower surfaces: Matte. Color: When opening, upper surface: Close to NN155D. When opening, lower surface: Close to NN155D tinged with close to 145C. Fully opened, upper surface: Close to NN155D; color does not change with development. Fully opened, lower surface: Close to NN155D; color does not change with development.

*Sepals, fertile flowers*.—Quantity and arrangement: Five in a single whorl. Length: About 1 mm. Width: About 1 mm. Shape: Deltoid. Apex: Acute. Base: Broadly cuneate. Margin: Entire. Texture, upper and lower surfaces: Smooth, glabrous. Luster, upper and lower surfaces: Matte. Color: When opening, upper and lower surfaces: Close to 157D. Fully opened, upper and lower surfaces: Close to 157D; color does not change with development.

*Pedicels, sterile flowers*.—Length: About 1.7 cm. Diameter: About 1 mm. Strength: Strong. Aspect: About 45° from peduncle. Texture: Moderately pubescent. Luster: Matte. Color: Proximally, close to NN155A; distally, close to NN155D.

*Pedicels, fertile flowers*.—Length: About 5 mm. Diameter: About 0.8 mm. Strength: Moderately strong. Aspect: Upright. Texture: Smooth, glabrous. Luster: Matte. Color: Close to 157D.

*Reproductive organs, sterile flowers*.—Stamens: Quantity per flower: Six to eight. Filament length: About 1 mm. Filament color: Close to NN155D. Anther shape: Broadly reniform. Anther length: About 0.4 mm. Anther color: Close to 155B. Pollen amount: Moderate. Pollen color: Close to 156D. Pistils: Pistil quantity per flower: Two. Pistil length: About 1 mm. Stigma shape: Club-shaped. Stigma color: Close to NN155A. Style length: About 0.5 mm. Style color: Close to NN155A. Ovary color: Close to 157D.

*Reproductive organs, fertile flowers*.—Stamens: Quantity per flower: Eight. Filament length: About 3 mm. Filament color: Close to NN155D. Anther shape: Broadly reniform. Anther length: About 0.4 mm. Anther color: Close to 155B. Pollen amount: Moderate. Pollen color: Close to 156D. Pistils: Pistil quantity per flower: Two. Pistil length: About 1 mm. Stigma shape: Club-shaped. Stigma color: Close to NN155A. Style length: About 0.5 mm. Style color: Close to NN155A. Ovary color: Close to 157D.

*Seeds*.—Seed development has not been observed on plants of the new *Hydrangea*.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'DICUR' as illustrated and described.

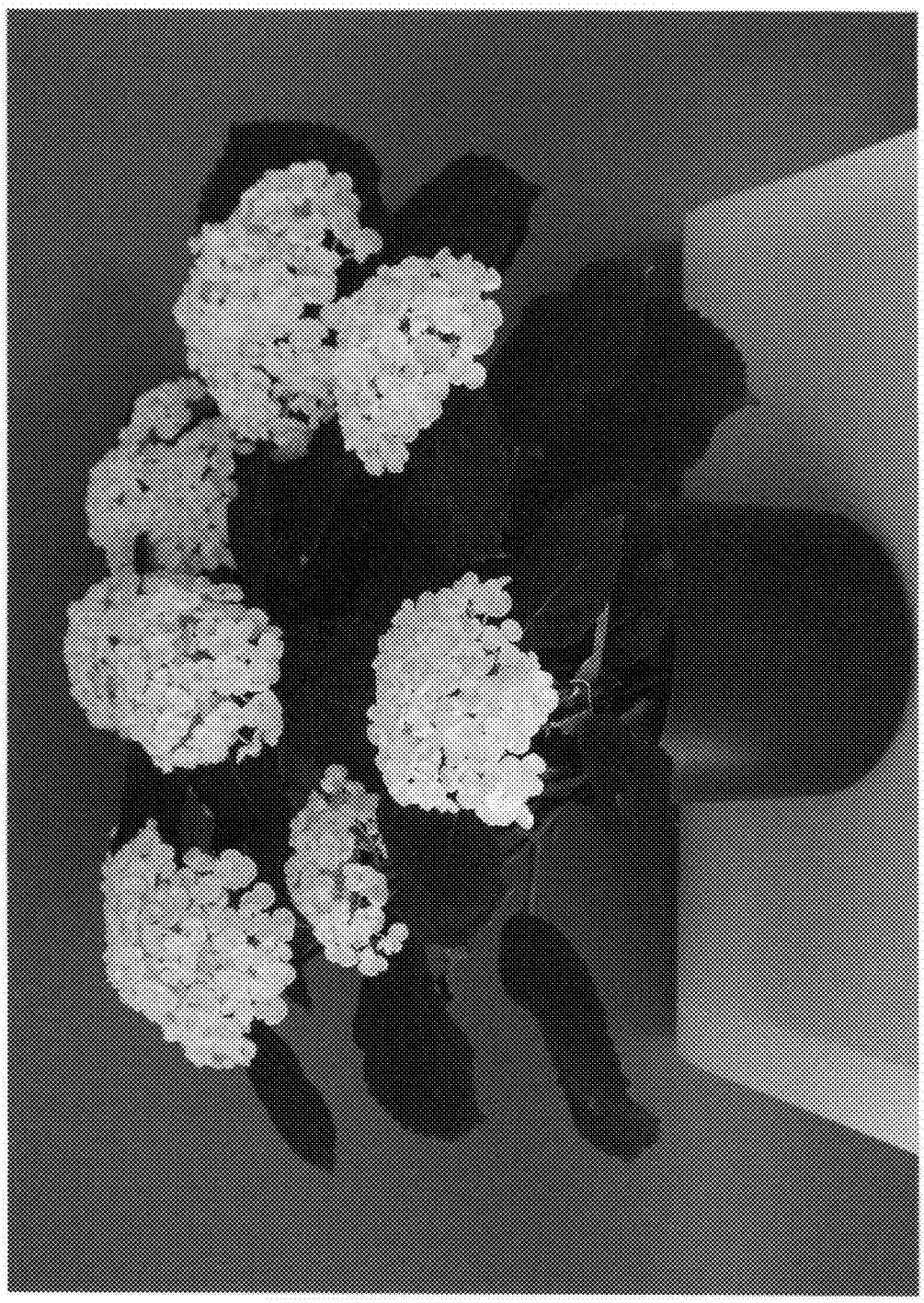

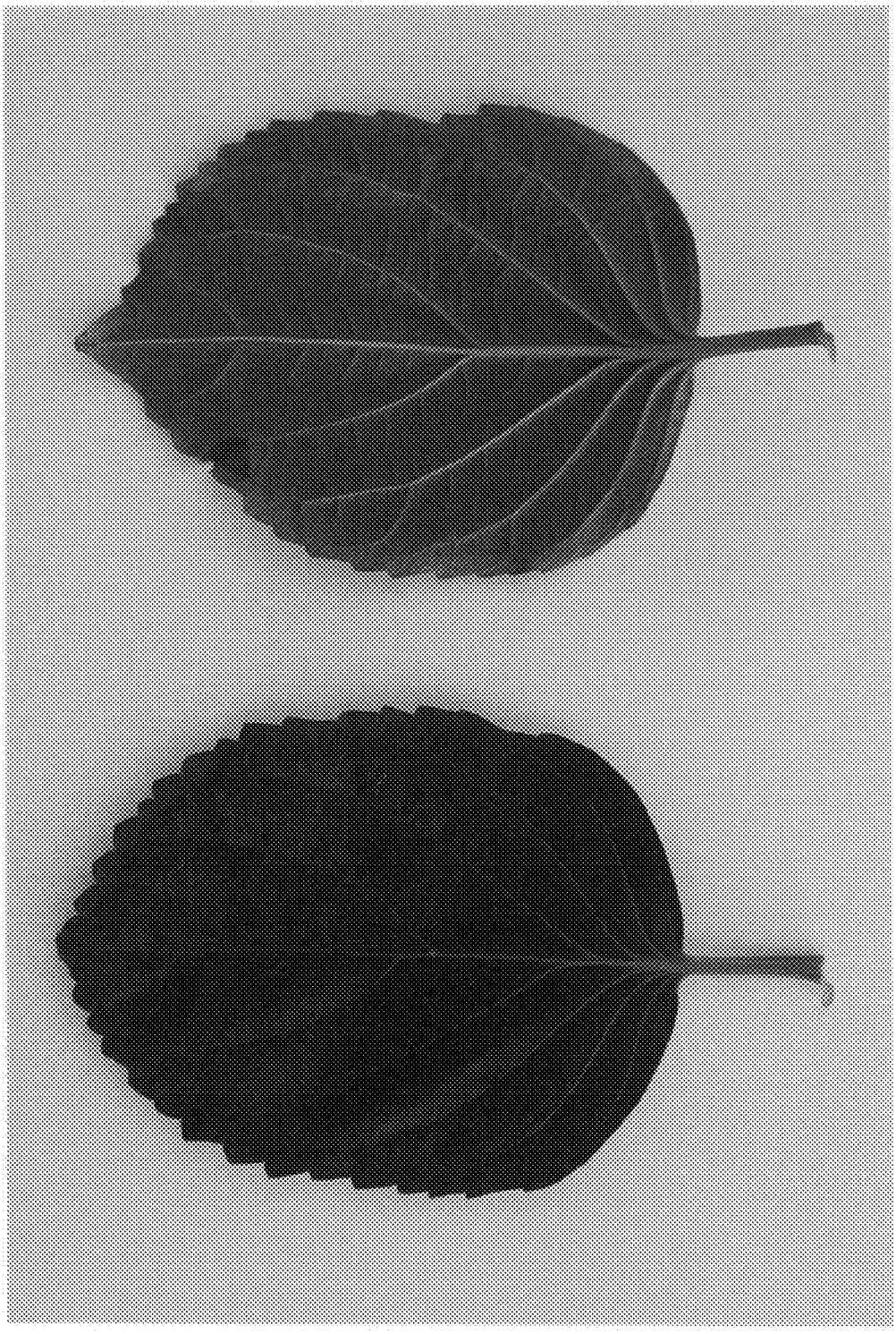

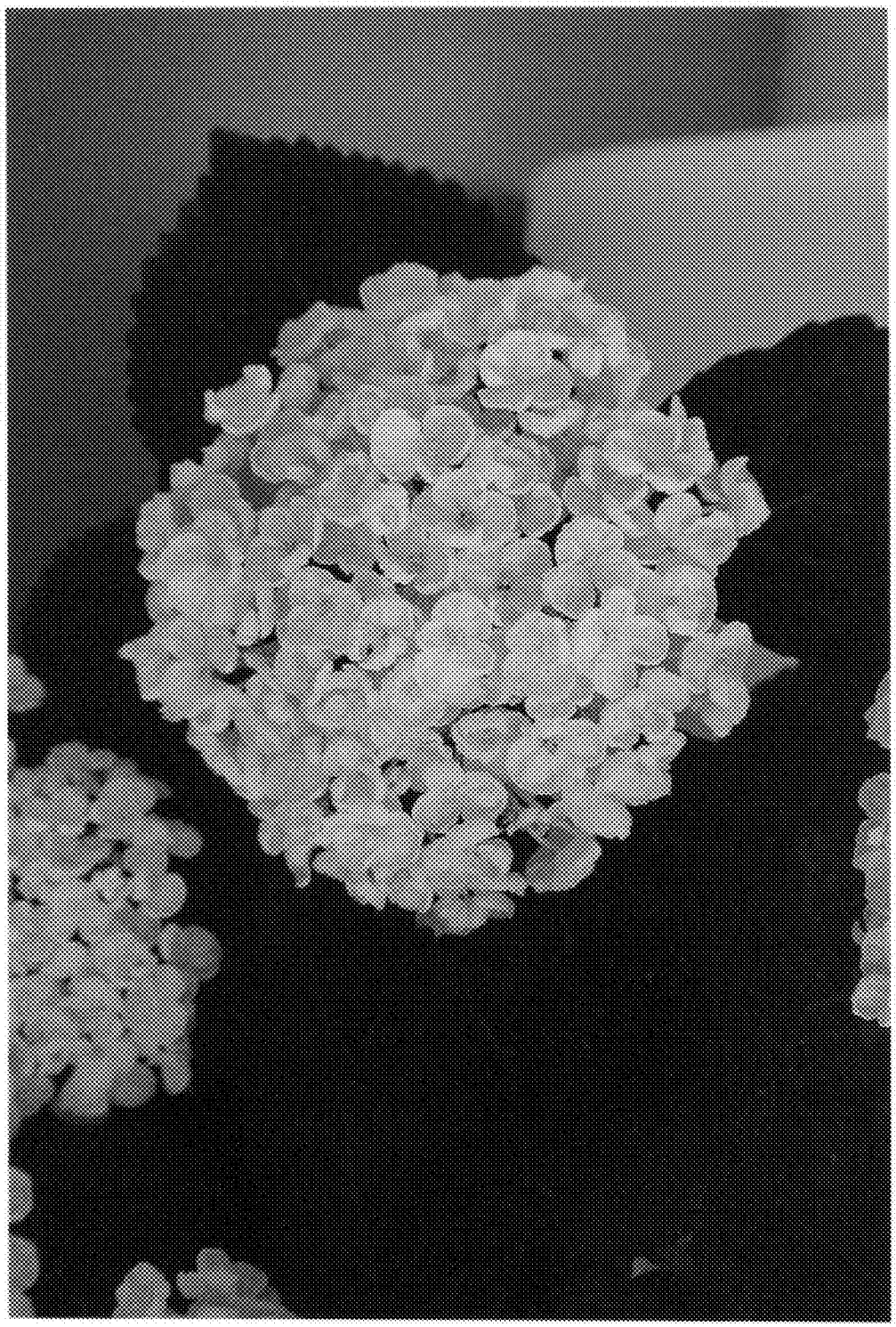

* * * * *